United States Patent
Lalonde et al.

(10) Patent No.: US 11,026,739 B2
(45) Date of Patent: Jun. 8, 2021

(54) THERMOCOUPLE-CONTROLLED CATHETER COOLING SYSTEM

(71) Applicant: Medtronic CryoCath LP, Toronto (CA)

(72) Inventors: Jean-Pierre Lalonde, Candiac (CA); Dan Wittenberger, L'Ile Bizard (CA); Marwan Abboud, Pierrefonds (CA); Constantin Bogdan Ciobotaru, St Dorothee (CA); Ramin Sabbaghe-Kermani, Laval (CA)

(73) Assignee: Medronic CryoCath LP, Toronto (CA)

( * ) Notice: Subject to any disclaimer, the term of this patent is extended or adjusted under 35 U.S.C. 154(b) by 613 days.

(21) Appl. No.: 15/919,782

(22) Filed: Mar. 13, 2018

(65) Prior Publication Data
US 2018/0235685 A1 Aug. 23, 2018

Related U.S. Application Data

(63) Continuation of application No. 14/706,289, filed on May 7, 2015, now Pat. No. 9,936,998, which is a
(Continued)

(51) Int. Cl.
*A61B 18/02* (2006.01)
*A61B 18/00* (2006.01)
*A61M 25/01* (2006.01)

(52) U.S. Cl.
CPC ...... *A61B 18/02* (2013.01); *A61B 2018/0022* (2013.01); *A61B 2018/00023* (2013.01);
(Continued)

(58) Field of Classification Search
CPC .......... A61B 18/02; A61B 2018/00023; A61B 2018/0022; A61B 2018/00797;
(Continued)

(56) References Cited

U.S. PATENT DOCUMENTS 3,791,387 A 2/1974 Itoh
4,022,215 A 5/1977 Benson
(Continued)

FOREIGN PATENT DOCUMENTS

EP 0624347 A1 11/1994
FR 2655836 A1 6/1991
(Continued)

OTHER PUBLICATIONS

International Search Report and Written Opinion dated Aug. 31, 2009, for corresponding International Application No. PCT/CA2009/000653; International Filing Date: May 14, 2009 consisting of 12-pages.

*Primary Examiner* — Daniel W Fowler
(74) *Attorney, Agent, or Firm* — Christopher & Weisberg, P.A.

(57) ABSTRACT

The present invention provides a medical system, including a catheter defining an injection lumen, a chamber in fluid communication with the injection lumen, and an exhaust lumen in fluid communication with the chamber; a first temperature sensor positioned in the exhaust lumen proximal to the chamber; a second temperature sensor positioned in the chamber; and a console in electrical communication with the first and second temperature sensors, the controller modifying coolant flow through the medical device based at least in part upon a signal received from the first and second temperature sensor. The system may further include a thermally-conductive element circumscribing a substantial portion of the exhaust lumen proximal to the chamber, where the first temperature sensor is mounted to the thermally-conductive element, and the thermally-conductive element may include at least one of a braid, coil, and band.

10 Claims, 3 Drawing Sheets

Related U.S. Application Data continuation of application No. 12/122,436, filed on May 16, 2008, now Pat. No. 9,050,069.

(52) U.S. Cl.
CPC ............. *A61B 2018/00797* (2013.01); *A61B 2018/00821* (2013.01); *A61B 2018/0212* (2013.01); *A61B 2018/0262* (2013.01); *A61M 25/0136* (2013.01)

(58) Field of Classification Search
CPC .. A61B 2018/00821; A61B 2018/0212; A61B 2018/0262
See application file for complete search history.

(56) References Cited

U.S. PATENT DOCUMENTS

| | | |
|---|---|---|
| 4,072,152 A | 2/1978 | Linehan |
| 4,699,147 A | 10/1987 | Chilson et al. |
| 4,758,221 A | 7/1988 | Jureidini |
| 4,819,655 A | 4/1989 | Webler |
| 4,930,494 A | 6/1990 | Takehana et al. |
| 5,010,894 A | 4/1991 | Edhag |
| 5,108,390 A | 4/1992 | Potocky et al. |
| 5,147,355 A | 9/1992 | Friedman et al. |
| 5,228,442 A | 7/1993 | Imran |
| 5,255,679 A | 10/1993 | Imran |
| 5,281,213 A | 1/1994 | Milder et al. |
| 5,281,215 A | 1/1994 | Milder |
| 5,293,869 A | 3/1994 | Edwards et al. |
| 5,327,889 A | 7/1994 | Imran |
| 5,345,936 A | 9/1994 | Pomeranz et al. |
| 5,400,783 A | 3/1995 | Pomeranz et al. |
| 5,405,671 A | 4/1995 | Kamin et al. |
| 5,423,807 A | 6/1995 | Milder |
| 5,465,717 A | 11/1995 | Imran et al. |
| 5,487,385 A | 1/1996 | Avitall |
| 5,549,661 A | 4/1996 | Kordis et al. |
| 5,582,609 A | 12/1996 | Swanson et al. |
| 5,647,871 A | 7/1997 | Levine et al. |
| 5,653,683 A | 8/1997 | D'Andrea |
| 5,680,860 A | 10/1997 | Imran |
| 5,694,646 A | 12/1997 | Roberts |
| 5,702,438 A | 12/1997 | Avitall |
| 5,730,704 A | 3/1998 | Avitall |
| 5,733,280 A | 3/1998 | Avitall |
| 5,738,683 A | 4/1998 | Osypka |
| 5,759,182 A * | 6/1998 | Varney ............... A61B 18/02 606/21 |
| 5,800,482 A | 9/1998 | Pomeranz et al. |
| 5,846,238 A | 12/1998 | Jackson et al. |
| 5,868,735 A | 2/1999 | Lafontaine |
| 5,899,898 A | 5/1999 | Arless et al. |
| 5,899,899 A | 5/1999 | Arless et al. |
| 5,957,963 A | 9/1999 | Dobak, III |
| 6,241,722 B1 * | 6/2001 | Dobak ............... A61B 18/02 606/20 |
| 6,270,476 B1 * | 8/2001 | Santoianni ......... A61B 18/02 600/585 |
| 6,471,693 B1 | 10/2002 | Carroll et al. |
| 6,514,245 B1 * | 2/2003 | Williams ............ A61B 18/02 128/898 |
| 6,551,309 B1 | 4/2003 | LePivert |
| 6,569,158 B1 | 5/2003 | Abboud et al. |
| 6,575,966 B2 | 6/2003 | Lane et al. |
| 6,589,234 B2 | 7/2003 | Lalonde et al. |
| 6,592,577 B2 | 7/2003 | Abboud et al. |
| 6,755,822 B2 | 6/2004 | Reu et al. |
| 6,796,979 B2 | 9/2004 | Lentz |
| 6,893,433 B2 | 5/2005 | Lentz |
| 7,285,118 B1 * | 10/2007 | Lozano ............ A61B 18/1492 128/898 |
| 2002/0007180 A1 | 1/2002 | Wittenberger et al. |
| 2002/0077625 A1 | 6/2002 | Lev |
| 2002/0115989 A1 | 8/2002 | Abboud et al. |
| 2003/0187428 A1 | 10/2003 | Lane et al. |
| 2003/0220634 A1 | 11/2003 | Ryba et al. |
| 2004/0186538 A1 | 9/2004 | Eshel |
| 2004/0243119 A1 | 12/2004 | Lane et al. |
| 2005/0021026 A1 | 1/2005 | Baily |
| 2005/0222556 A1 | 10/2005 | Ariura et al. |
| 2006/0030843 A1 | 2/2006 | Lane et al. |
| 2006/0129142 A1 | 6/2006 | Reynolds |
| 2006/0259023 A1 | 11/2006 | Abboud et al. |
| 2007/0032783 A1 * | 2/2007 | Abboud ............ A61B 18/1492 606/21 |

FOREIGN PATENT DOCUMENTS

| | | |
|---|---|---|
| WO | 9804221 A1 | 2/1998 |
| WO | 0042932 A1 | 7/2000 |
| WO | 0152728 A1 | 7/2001 |
| WO | 2006119615 A1 | 11/2006 |

\* cited by examiner

THERMOCOUPLE-CONTROLLED CATHETER COOLING SYSTEM

CROSS-REFERENCE TO RELATED APPLICATION

This application is a continuation of and claims priority to U.S. patent application Ser. No. 14/706,289, filed May 7, 2015, entitled THERMOCOUPLE-CONTROLLED CATHETER COOLING SYSTEM, which is a continuation of and claims priority to U.S. patent application Ser. No. 12/122,436, filed May 16, 2008, entitled THERMOCOUPLE-CONTROLLED CATHETER COOLING SYSTEM, issued as U.S. Pat. No. 9,050,069, the entirety of all of which is incorporated herein by reference.

STATEMENT REGARDING FEDERALLY SPONSORED RESEARCH OR DEVELOPMENT n/a

TECHNICAL FIELD

The present invention relates to a method and system for controlling fluid flow in a medical device, and in particular, towards controlling the flow of a coolant in an intravascular catheter via temperature feedback.

BACKGROUND

The use of fluids with low boiling temperatures, or cryogens, is becoming increasingly explored and employed in the medical and surgical field. Of particular interest is the use of catheter based devices employing the flow of cryogenic fluids therein to selectively freeze or otherwise thermally affect targeted tissues within the body. Catheter based devices are desirable for various medical and surgical applications in that they are relatively non-invasive and allow for precise treatment of localized discrete tissues that are otherwise inaccessible. Catheters may be easily inserted and navigated through the blood vessels and arteries, allowing non-invasive access to areas of the body with relatively little trauma.

Catheter-based ablation systems are well known in the art. A cryogenic device uses the energy transfer derived from thermodynamic changes occurring in the flow of a cryogen therethrough to create a net transfer of heat flow from the target tissue to the device, typically achieved by cooling a portion of the device to very low temperature through conductive and convective heat transfer between the cryogen and target tissue. The quality and magnitude of heat transfer is regulated by the device configuration and control of the cryogen flow regime within the device.

A cryogenic device uses the energy transfer derived from thermodynamic changes occurring in the flow of a refrigerant through the device. This energy transfer is then utilized to create a net transfer of heat flow from the target tissue to the device, typically achieved by cooling a portion of the device to very low temperature through conductive and convective heat transfer between the refrigerant and target tissue. Structurally, cooling can be achieved through injection of high pressure refrigerant through an orifice. Upon injection from the orifice, the refrigerant undergoes two primary thermodynamic changes: (i) a depressurization (adiabatic) and temperature drop through positive Joule-Thomson throttling, and (ii) undergoing a phase change from liquid to vapor, as the fluid absorbs heat. The resultant flow of low temperature refrigerant through the device acts to absorb heat from the target tissue and thereby cool the tissue to the desired temperature.

Presently available cooling systems typically operate based upon a set coolant flow rate or coolant pressure in the catheter or medical device that is used to reach a desired temperature for treatment. A measurement of the flow rate or pressure may be used in a feedback loop to control a pump or other component controlling the actual coolant flow. However, depending on the thermal load experienced by a particular device as well as the particular target temperature trying to be reached, there can be significant thermal variations for a predetermined flow or pressure value at different portions of a medical device having fluid flow therethrough. For example, for a fixed flow rate and a low thermal load on a device, a flow rate may become excessive, resulting in a portion of the circulating fluid failing to change phase from a liquid/solid to a gas, and thereby reducing the overall thermal efficiency and affect on the surrounding tissue. Moreover, at a high heat load, a set flow rate may not sufficiently provide a treatment area on the device having the desired temperature, i.e., the temperature may vary drastically from one location to the next despite the proximity of the two locations because of the temperatures trying to be achieved and the thermal energy/load surrounding a particular device. As a result, the actual tip or device temperature may be different than a target temperature correlating to a set flow or pressure due to thermal variations at the treatment site.

Accordingly, it would be desirable to provide an improved apparatus and method of monitoring and controlling the circulation of a coolant through a medical device such as an intravascular catheter.

SUMMARY

The present invention advantageously provides a method and system including a medical device having an injection lumen; a chamber in fluid communication with the injection lumen; an exhaust lumen in fluid communication with the chamber; a thermally-conductive element circumscribing (or otherwise disposed about) a substantial portion of the exhaust lumen proximal to the chamber; and a first temperature sensor mounted on the thermally conductive element. The thermally-conductive element can include at least one of a braid, coil, and band. The device may also include a second temperature sensor positioned in the chamber, as well as a console in electrical communication with the first and second temperature sensors, the controller modifying coolant flow through the medical device based at least in part upon a signal received from the first and/or second temperature sensor. The console may include a coolant supply in fluid communication with the injection lumen and a vacuum source in fluid communication with the exhaust lumen.

The present invention also includes an intravascular catheter system, including a catheter defining an injection lumen, a chamber in fluid communication with the injection lumen, and an exhaust lumen in fluid communication with the chamber; a first temperature sensor positioned in the exhaust lumen proximal to the chamber; a second temperature sensor positioned in the chamber; and a console in electrical communication with the first and second temperature sensors, the controller modifying coolant flow through the medical device based at least in part upon a signal received from the first and/or second temperature sensor. A thermally-conductive element may circumscribe a substantial portion of the exhaust lumen proximal to the chamber, and the first temperature sensor may be mounted to the thermally-conductive element. The system may also include multiple temperature sensors coupled to multiple thermally-conductive elements positioned along a substantial length of the medical device.

The present invention also provides a method for controlling fluid flow through a medical device, including circulating a coolant through the medical device; measuring a first temperature at a distal portion of the medical device; measuring a second temperature at a position proximal of the distal portion of the medical device; and adjusting the circulation of coolant based at least in part upon the first and second temperature measurements. The method may also include determining a pressure measurement or value based upon at least one of the first and second temperature measurements. Further, the first temperature measurement may be performed by a first temperature sensor, and the second temperature measurement may be performed by a second temperature, the method further including measuring an electrical resistance or impedance between the first and second temperature sensors; and determining the presence of a leak in the medical device based at least in part upon the measured electrical value or property. The method may also include thermally affecting a target tissue with the medical device, where thermally affecting the target tissue includes ablating cardiac tissue.

Presence of a leak may also be determined by measuring the temperature using one or more of the sensors described above. For example, liquid that might enter the device evaporates under vacuum, thereby causing a measurable temperature variation. As such, the method may also include correlating at least one of the first and second measured temperatures to a leak condition of the medical device, and/or correlating a difference between the first and second measured temperatures to a leak condition of the medical device. The correlation of a leak may be based on one or more temperature measurements taken before, during, and/or after any cooling fluid is introduced or otherwise circulated through the device.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
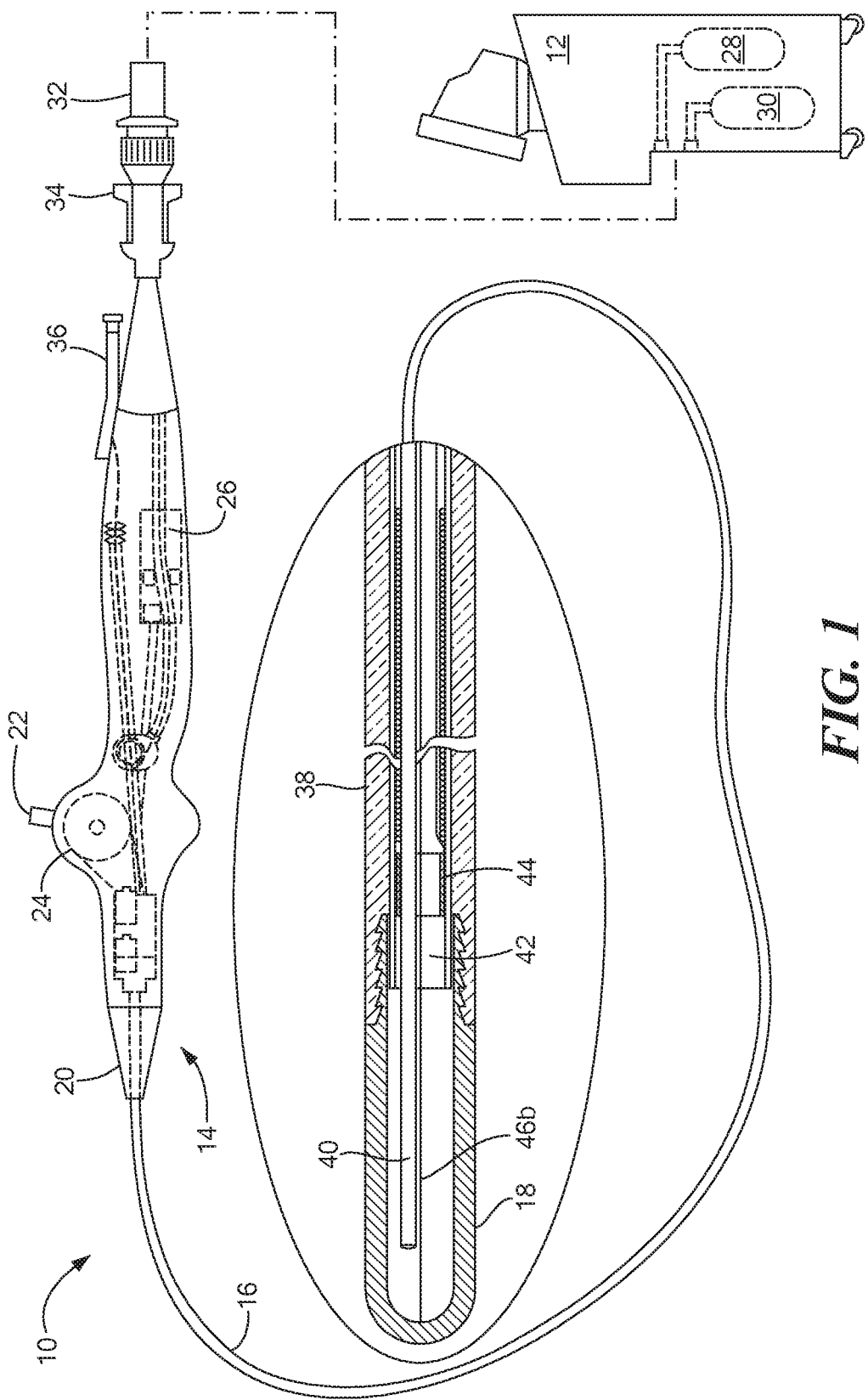
FIG. 1 is an embodiment of an exemplary medical treatment system constructed in accordance with the principles of the present invention.

The present invention provides an improved apparatus and method of monitoring and controlling the circulation of a coolant through a medical device such as an intravascular catheter or surgical probe. Referring now to the drawing figures in which like reference designators refer to like elements, there is shown in FIG. 1 an exemplary system suitable for thermally treating tissue, generally designated as 10. The system 10 includes a console 12 coupled to a medical treatment device 14, where the treatment device 14 may be a medical probe, a catheter, a balloon-catheter, as well as other devices commonly known in the art, such as devices able to pass easily through blood vessels and heart valves and able to thermally affect tissue, for example. Of course, the present invention is compatible with catheters or probes that are equally adaptable for both endovascular and surgical procedures involving thermal treatment applications.

In particular, the system 10 may include an elongate, highly flexible catheter that is suitable for passage through the vasculature. The medical treatment device 14 may thus include a catheter body 16 having a distal end with a treatment element 18 or region at or proximal to the distal end. The catheter body 16 may also define one or more lumens disposed within the catheter body 16 thereby providing mechanical, electrical, and/or fluid communication between the proximal portion of the elongate body and the distal portion of the elongate body. In addition, the catheter body 16 may include a guidewire lumen (not shown) extending along at least a portion of the length of the catheter body 16 for over-the-wire applications. The guidewire lumen may be movably disposed within at least a portion of the catheter body 16 such that a distal end of the guidewire lumen extends beyond the and out of the distal portion of the catheter body 16.

The catheter body 16 has a proximal end that is mated to a handle 20, and the handle 20 can include an element such as a lever or knob 22 for manipulating or deflecting at least a portion of the catheter body 16. In the exemplary embodiment, a pull wire having a proximal end and a distal end has its distal end anchored to the catheter body 16 and/or treatment element 18 at or near the distal end. The proximal end of the pull wire is anchored to an element such as a cam 24 in communication with and responsive to the lever 22. The handle 20 can further include circuitry 26 for identification and/or use in controlling of the ablation catheter or another component of the system 10.

Continuing to refer to FIG. 1, the handle 20 can also include connectors that are matable directly or indirectly by way of one or more umbilicals to the console 12 and a coolant or fluid supply 28, vacuum source unit 30, and/or electronics therein. For example, in the illustrated system 10, the handle 20 is provided with a first connector 32 that is matable with a co-axial fluid umbilical (not shown) and a second connector 34 that is matable with an electrical umbilical (not shown) that can further include an accessory box (not shown). The handle 20 may also be provided with a fitting 36 for receiving a guide wire (not shown) that is passed into the guide wire lumen. The handle 20 may also include one or more pressure, temperature, flow rate, and/or other sensors to monitor the desired characteristics and performance parameters of the system 10.

The console 12 provides the user interface to the system 10 and houses the electronics and software for controlling and recording a selected procedure, controlling the delivery of the liquid refrigerant under pressure through the umbilical to the treatment device 14, controlling the recovery of the expanded refrigerant vapor from the treatment device 14 under vacuum, and for optionally controlling a compressor if present to pressurize the coolant vapor into a liquid stored in a recovery tank (not shown).

As stated above, the console 12 may include the vacuum pump 30 or source unit in fluid communication with the medical treatment device 14. The vacuum pump 30 is controllable to reduce the pressure within a portion, such as an exhaust fluid flow path, of the medical treatment device 14 to provide a pressure ranging from a pure vacuum to a pressure just below a patient's blood pressure. For example, the vacuum pump 30 can maintain a selected pressure between 80 mm Hg and 0 mm Hg prior to injection. The provision of reduced pressure within a return flow path of the catheter body 16 of the treatment device 14 significantly enhances patient safety because, should a leak occur, refrigerant or coolant will not flow from the device into the patient. Rather, bodily fluids in the treatment site will be aspirated into the catheter body 16 whereupon they may be sensed by leak detection elements and initiate a cascade of pre-programmed events. In particular, either or both of the treatment device 14 and the console 12 can be provided with detection devices that are in electrical communication with the console 12 and which may provide a signal output that can be representative of an event that indicates flow path integrity loss or a leak within a sealed portion of the surgical device and/or console 12. The console 12 can be configured to respond to signal output from the one or more sensors or detectors and initiate a predetermined sequence of events, such as discontinuing refrigerant injection, changing the pressure or flow rate within the system 10, and/or controlling removal of refrigerant from the catheter body 16.

In addition to providing an exhaust function for the fluid in the medical treatment device 14, the console 12 can also recover and/or recirculate the cooling fluid. In addition, console 12 can include an LCD touch screen that displays console status and data, and accepts user data and control inputs. Various discrete indicators, controls, and displays may also be included which indicate the status of one or more console parameters and allow inputs for manual system 10 operation.

Figure 2:
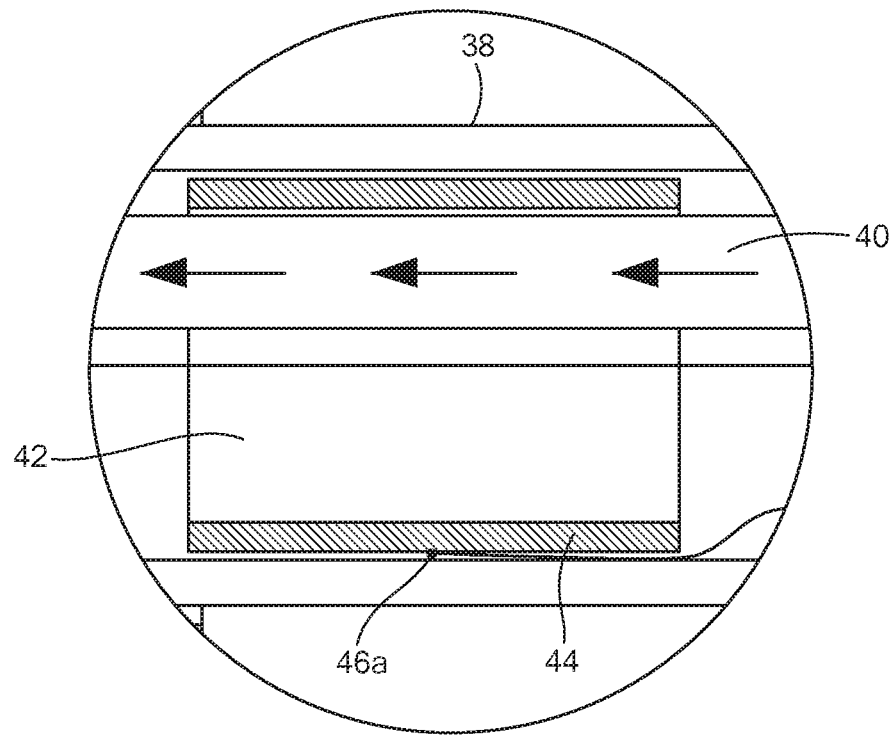
FIG. 2 is a magnified image of a portion of the medical device illustrated in FIG. 1.

Now referring to FIGS. 1 and 2, the distal end of the medical treatment device 14 is shown. The distal end or region of the medical device may include the thermally-transmissive or conductive treatment element 18 coupled to an insulated or otherwise less thermally-conductive shaft portion 38 of the medical device body 16. For example, the distal region may include a metallic tip, a conductive balloon (not shown) or the like defining a chamber receiving coolant flow for enhanced thermal interaction with a target tissue. A coolant supply tube 40 defining a fluid supply lumen may be included in fluid communication with the coolant supply 28 in the console 12. The coolant supply tube 40 may include one or more openings able to disperse a provided fluid or coolant within and/or proximate to the distal region and the treatment element 18 of the device 14 in response to console 12 commands and other control input. The medical treatment device 14 may further include a coolant exhaust or return lumen 42, which may be defined at least in part by the medical device body 16. The vacuum pump 30 in the console 12 may be in fluid communication with the exhaust/return lumen 42 to create a pressure gradient within the medical device 14 so that coolant is drawn away from the distal tip and toward the proximal end of the medical device body 16.

The distal region of the medical device 14 may further include one or more reinforcement or structural elements 44 such as coils, braids, rings, or the like embedded, positioned, and/or otherwise coupled to a portion of the medical device body. The reinforcement elements 44 may be directly exposed to or otherwise be in thermal communication with the exhaust lumen 42 of the medical device 14, and may be constructed from a metallic material for example. The reinforcement elements 44 may circumscribe all of and/or a substantial portion of the circumference of the medical device body 14, and may further extend along a substantial length of the medical device body 16 from a position just proximal to or adjacent to the treatment element 18 to a proximal end of the device near the handle 20.

The medical treatment device 14 may further include one or more temperature sensors positioned in thermal communication with the exhaust lumen, and in particular, may be exposed to fluid flow therethrough or otherwise in thermal communication with the thermally-transmissive element(s). The temperature sensors may include thermocouples, thermistors, or other temperature-sensitive device or element as known in the art. For example, the medical treatment device 14 may include a first temperature sensor 46a mounted on or otherwise connected to a reinforcement element 44 such as conductive band or ring circumscribing at least a portion of the circumference of the exhaust lumen 42 in a region of the medical device body 16 proximal to the treatment element 18, where the conductive band/ring may be constructed from a metallic or otherwise thermally-conductive material. Alternatively, the first temperature sensor 46a may be mounted on or otherwise connected to one or more of the reinforcement elements 44 such as a coil or braid positioned along a length of the medical device body proximal to the treatment element 18.

The medical device 14 may further include one or more temperature sensors such as a thermocouple, thermistor, or other temperature-sensitive device or element disposed within or otherwise mounted on the treatment element 18. For example, a second temperature sensor 46b may be positioned adjacent to one or more openings in the coolant supply tube 40 for measurement and/or monitoring of thermal characteristics in the region. The one or more temperature sensors of the medical device 14 may be electrically coupled to or otherwise in communication with the console 12 for sending signals corresponding to measured or sensed temperatures thereto, which may impact or otherwise affect control of fluid flow therethrough.

Figure 3:
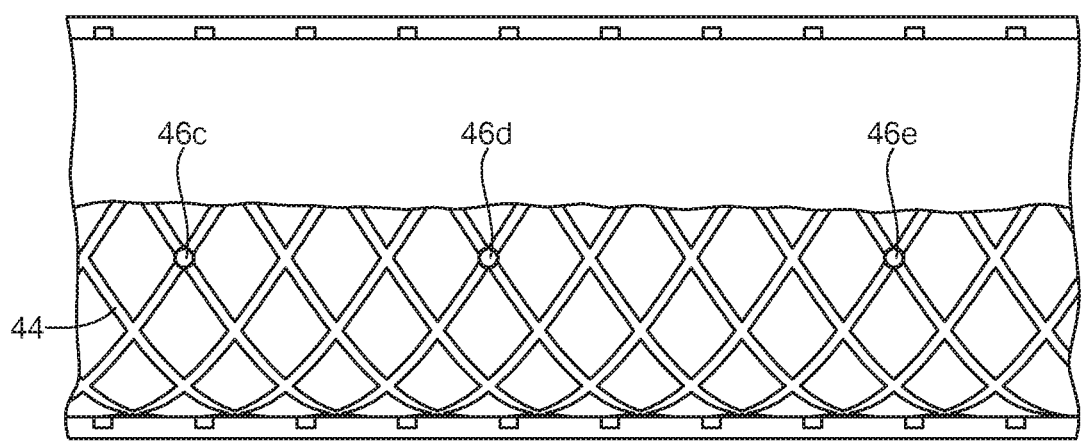
FIG. 3 is an illustration of a portion of an embodiment of a medical device constructed in accordance with the principles of the present invention.
Figure 4:
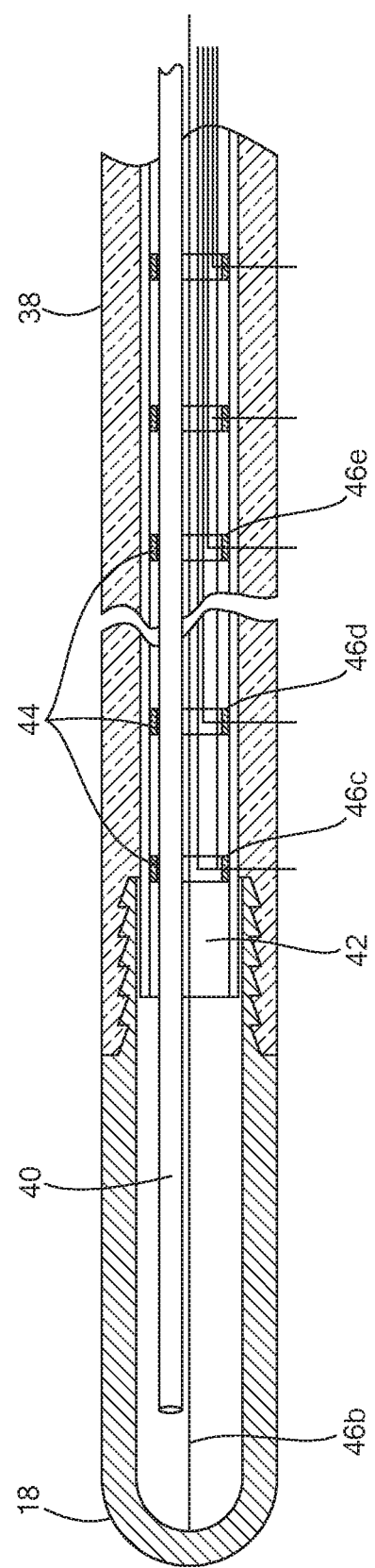
FIG. 4 is an embodiment of an exemplary medical device constructed in accordance with the principles of the present invention.

Now referring to FIGS. 3 and 4, the medical treatment device 14 may include multiple temperature sensors 46c, 46d, 46e . . . etc. (collectively referred to as "46") disposed along the length of the medical device 14 and/or catheter body 16, where the multiple temperature sensors 46 are intermittently positioned to provide information about the thermal characteristics and environment at discrete locations of the medical device 14 in order to more effectively control cooling and treatment. For example, as shown in FIG. 3, the multiple temperature sensors 46 may be coupled to or otherwise mounted on intersecting segments of a support element 44 such as a braid, which as discussed above, may be thermally conductive and constructed from a metallic material. As shown in FIG. 4, the temperature sensors 46 may be coupled to reinforcement elements 44 such as rings or bands intermittently located along the length of the medical device body 16 to similarly provide information at discrete locations of the device. As described above, each of the temperature sensors may be electrically coupled to and/or otherwise in communication with the console 12 to aid in regulating and controlling characteristics of coolant flow through the medical treatment device 14.

In an exemplary method of use for the system 10 described above and shown in FIGS. 1-4, a user may employ the system 10 for a thermal treatment of desired tissue. For example, an ablation and/or mapping procedure on cardiac tissue may be desirable, and as such, may be executed through manipulation of the medical treatment device 14 and the controls of the console 12. In particular, the treatment may include the initiation of coolant flow through the medical device and the treatment tip, which may be achieved through pressurization of the coolant form the coolant supply and/or manipulation of the operation of the vacuum pump to provide the desired flow rate, pressure level, and/or resulting temperature characteristics at the tip. The coolant may include a combination of various gases and liquids including but not limited to argon, carbon dioxide, nitrous oxide, liquid nitrogen or the like. Should pressurized gas or liquid be delivered, the coolant may become depressurized and/or otherwise expand in the treatment tip, and a resulting phase-change provides a reduced temperature for thermally affecting the tissue.

During the circulation of coolant through the medical treatment device 14, measured temperature values from at least the first and second temperature sensors located in the exhaust path 42 and the treatment element 18, respectively, may be relayed or otherwise monitored at the console 12. As discussed above, there may be significant discrepancies between a temperature in the treatment element 18 where the coolant expansion may occur, and a portion of the exhaust path 42 just proximal of the distal treatment tip. For example, it has been found that temperature differences between the tip where the coolant expansion may occur and a portion of the exhaust path 42 just fractions of an inch proximal of the treatment element 18 can be as much as twenty degrees Celsius or more. The significant discrepancies may result in a failure of the coolant to provide optimal cooling in the thermal interaction between the treatment device 14 and the target tissue.

The resulting signals conveyed to the console 12 by the two temperature sensors may be used to adjust, regulate, or otherwise control fluid flow through the treatment device 14. For example, if it is found that the temperature in the tip is sufficient for treatment, but the temperature in the return path 42 is too low and/or the coolant is not completely changing phase, the flow rate and/or pressure of the coolant in the medical treatment device 14 may be adjusted accordingly at or by the console 12. By adjusting a flow rate and/or pressure of the coolant circulation based upon multiple temperature sensor signals, a more accurate and efficient cooling treatment process may be achieved without wasting coolant or otherwise failing to optimally deliver the desired thermal treatment.

In addition to monitoring signals from the first and second temperature sensors to adjust flow, in an embodiment where there are a plurality of temperature sensors 46 intermittently disposed along the length of the shaft, as discussed above with respect to FIGS. 3 and 4, the signals from the plurality of sensors may be used to map or otherwise monitor thermal characteristics occurring at discrete positions along the length of the device 14, and flow rates/pressures may be adjusted accordingly. The temperature sensors provide a more complete picture of the thermal behavior of the device and the coolant circulation path under varying heat loads. For example, depending on the length of a particular catheter and/or the depth of insertion into a patient, the thermal loads will vary significantly along the length of the catheter body, i.e., the portion of the device outside of the body versus the portion inside, and these variations may be monitored and provide a basis for adjustment during a treatment procedure.

Of note, the output or measurement signals of the one or more temperature sensors 46 of the medical treatment device may also be used to determine a pressure of coolant at that particular point in the device. In particular, a temperature value of a fluid at saturation can be directly correlated to a pressure. For example, if particular physical properties of the coolant being used are known, then a temperature measurement of that substance under saturation can be used to determine a resulting pressure level. As such, one or more temperature sensors may be able to provide the function of delivering both a direct temperature reading as well as forming the basis for a calculated pressure value given known physical properties of the coolant. In a particular example, a saturation pressure is proportional to the saturation temperature.

In an additional method of use for the system and components described above, two or more of the temperature sensors 46 may be employed to provide for the detection and resulting indication of a leak in a portion of the medical device. In particular, two of the temperature sensors, which may include thermocouples, may be electrically isolated and have a common ground. In addition to monitoring the signals indicative of temperature measurements by the temperature sensors, a resistance or impedance between the two temperature sensors can be monitored and changes thereof can indicate a leak. In particular, when a leak occurs and fluid form the surrounding tissue is entrained into the exhaust path (which is under vacuum). The entrained liquid may evaporate, and thus cause localized cooling, which can be indicated by a temperature sensor in proximity to the leak by having a different value than the surrounding sensors. In addition, the entrained fluid changes the electrical value between two or more of the temperature sensors, and thus the change in resistance, impedance or the like can also indicate the presence of a leak or breach of the structural integrity of the fluid flow path.

By employing the existing or present temperature sensors to detect a leak, there is no need for additional leak detection apparatus, which may take up space in a small dimensioned medical device, add to manufacturing cost, etc. Moreover, monitoring temperature provides a leak detection apparatus that does not require the use of high frequency circuits as with impedance leak detection circuit schemes presently known in the art. In addition, the cables or wires of the temperature sensors may be braided or shielded to eliminate electrical cross-talk or interference with the surrounding environment, such as a radiofrequency generator used in the vicinity.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical system, the system comprising:
  a catheter having a length and defining an injection lumen, a chamber in fluid communication with the injection lumen, and an exhaust lumen in fluid communication with the chamber;
  a thermally conductive reinforcement element disposed within the catheter and circumscribing a substantial portion of the exhaust lumen, the reinforcement element extending along a substantial length of the exhaust lumen;
  a plurality of temperature sensors coupled to the reinforcement element;

a cryogenic fluid supply in fluid communication with the injection lumen, the reinforcement element being directly exposed to cryogenic fluid within the exhaust lumen and; and a console in electrical communication with the plurality of temperature sensors, the console being programmed to:
  receive temperature measurements from each of the plurality of temperature sensors;
  determine temperature characteristics at a plurality of discrete locations along the length of the catheter;
  calculate a pressure of the cryogenic fluid at each of the plurality of discrete locations along the length of the catheter; and
  adjust a flow of the cryogenic fluid within the catheter based on the calculated pressure at each of the plurality of discrete locations along the length of the catheter.

2. The system of claim 1, wherein the reinforcement element circumscribes an inner circumference of the exhaust lumen.

3. The system of claim 2, wherein the exhaust lumen has a length, the reinforcement element extending along an entirety of the length of the exhaust lumen.

4. The system of claim 1, wherein the reinforcement element is located entirely within the exhaust lumen.

5. The system of claim 1, wherein the reinforcement element includes at least one of a braid and a coil.

6. The system of claim 3, wherein the reinforcement element is a braid having a plurality of intersecting segments defining a plurality of intersecting points, each of the plurality of temperature sensors being at a corresponding one of the plurality of intersecting points.

7. The system of claim 1, further comprising a vacuum source in fluid communication with the exhaust lumen.

8. The system of claim 7, wherein the vacuum source maintains a pressure within the exhaust lumen to a pressure between 80 mm Hg and 0 mm Hg before an initiation of the flow of cryogenic fluid within the catheter.

9. A method of using a medical system, the method comprising:
  circulating a cryogenic fluid through a catheter having a length and including:
    an injection lumen;
    a chamber in fluid communication with the injection lumen;
    an exhaust lumen in fluid communication with the chamber;
    a thermally conductive braid disposed within and circumscribing a substantial portion of the exhaust lumen, the braid including a plurality of intersecting segments defining a plurality of intersecting points; and
    a plurality of temperature sensors coupled to the thermally conductive braid, each of the plurality of temperature sensors being at a corresponding one of the plurality of intersecting points;
  receiving temperature measurements from each of the plurality of temperature sensors;
  determining temperature characteristics at a plurality of discrete locations along the length of the catheter;
  calculating a pressure of a cryogenic fluid at each of the plurality of discrete locations along the length of the catheter; and
  adjusting a flow of the cryogenic fluid within the catheter based on the calculated pressure at each of the plurality of discrete locations along the length of the catheter.

10. The method of claim 9, further comprising maintaining with a vacuum source a pressure within the exhaust lumen to a pressure between 80 mm Hg and 0 mm Hg before an initiation of the flow of cryogenic fluid within the catheter.

* * * * *